United States Patent [19]

He et al.

[11] Patent Number: 5,828,719
[45] Date of Patent: Oct. 27, 1998

[54] METHODS AND APPARATUS FOR MODULATING DATA ACQUISITION SYSTEM GAIN

[75] Inventors: Hui David He; Gary Richard Strong, both of Waukesha; Thomas Louis Toth, Brookfield; George E. Seidenschnur, Waukesha, all of Wis.

[73] Assignee: General Electric Company, Milwaukee, Wis.

[21] Appl. No.: 779,961

[22] Filed: Dec. 23, 1996

[51] Int. Cl.[6] .................................................. A61B 6/03
[52] U.S. Cl. .................................................. 378/4; 378/901
[58] Field of Search ........................................ 378/4, 901

[56] References Cited

U.S. PATENT DOCUMENTS 5,473,656  12/1995  Hsieh et al. ............................. 378/4
5,528,644  6/1996  Ogawa et al. ......................... 378/901

Primary Examiner—Don Wong
Attorney, Agent, or Firm—John S. Beulick; John H. Pilarski

[57] ABSTRACT

The present invention, in one form, is a system which, in one embodiment, varies DAS gain to better accommodate different scanning parameters between different scans, even at the same slice thickness. Specifically, in one embodiment, the DAS gain is varied, or modulated, as a function of slice thickness, x-ray tube current and voltage levels, scan time, and average detector gain. The DAS gain is modulated using a gain factor Gain_Fac which is determined in accordance with each of the above-mentioned scanning parameters. The gain factor Gain_Fac is then used to determine an appropriate DAS gain for such parameters. Particularly, DAS gains are stored in a look-up table in the CT system computer, and the gain factor Gain_Fac is used to select the appropriate DAS gain from the look-up table. The determined DAS gain is then utilized to correct data acquired during a scan.

17 Claims, 3 Drawing Sheets

| GAIN_FAC RANGE | 0-0.1 | >0.1 | >0.2 | >0.3 | >0.4 | >0.55 | >0.9 | >1.2 |
|---|---|---|---|---|---|---|---|---|
| DAS GAIN /$C_{int}$(pF) | 20 | 40 | 60 | 80 | 120 | 150 | 230 | 290 |
| DAS FULL-SCALE (nA) 984 VIEWS/s | 80 | 161 | 241 | 321 | 482 | 602 | 923 | 1164 |
| DAS FULL-SCALE (nA) 1405 VIEWS/s | 116 | 231 | 347 | 463 | 694 | 867 | 1330 | 1677 |

FIG. 4

METHODS AND APPARATUS FOR MODULATING DATA ACQUISITION SYSTEM GAIN

FIELD OF THE INVENTION

This invention relates generally to computed tomography (CT) imaging and more particularly, to calibrating a Data Acquisition System in a CT system.

Background of the Invention

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts that attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed.

Certain scanning parameters, such as x-ray tube current ("mA"), x-ray tube supply voltage ("kV"), slice thickness, scan time, and average detector gain are known to affect detector signal strength, which relates directly to image quality. With respect to x-ray tube current, for example, a higher x-ray tube current level typically produces a higher magnitude detector signal which typically generates images with less noise. Conversely, lower x-ray tube current levels are known to produce lower magnitude detector signals which are known to cause sever streaking artifacts in the resulting image.

To improve image quality even with low magnitude signals, known CT systems include a data acquisition system (DAS) which samples the analog signals produced by the detector elements, and converts such signals to digital signals for subsequent processing. The selection of the DAS gain includes a trade-off between low signal noise performance and potential overranging. Particularly, higher system gain improves low signal image quality by reducing streak artifacts and noise. Higher system gains also can result, however, in DAS overrange which produces shading and streak artifacts.

To reduce the likelihood of DAS overrange, the DAS gain is usually set to a low gain. While setting DAS gain to a low gain reduces DAS overrange, the low gain setting also typically increases electronic noise and image artifacts with low magnitude detector signals. Furthermore, once a DAS gain is selected and designed into a CT system, the DAS gain cannot easily be modified. Accordingly, and since CT systems are used with varying x-ray tube currents, x-ray tube supply voltages, slice thicknesses, and scan times, the selected DAS gain may be less than optimal for some scans.

In one known CT multi-slice system, DAS gains are modified, i.e., changed, for varying detector slice thicknesses. Specifically, for a scan with a predetermined detector slice thickness, a respective DAS gain is selected. The selected DAS gain then is used in connection with each scan at such thickness. However, the selected DAS gain may not be optimal over the entire slice for all scanning cases. Particularly, and as described above, scanning parameters other than slice thickness also affect signal strength, and thus appropriate DAS gain.

Accordingly, it would be desirable to provide an algorithm to facilitate modifying DAS gain that is not limited to detector slice thickness. It also would be desirable for such algorithm to facilitate modifying DAS gain on a scan-by-scan basis. It further would be desirable to provide such an algorithm which does not significantly increase the processing time.

SUMMARY OF THE INVENTION

These and other objects may be attained in a system which, in one embodiment, varies DAS gain to better accommodate different scanning parameters between different scans, even at the same slice thickness. Specifically, in one embodiment, the DAS gain is varied, or modulated, as a function of slice thickness, x-ray tube current and voltage levels, scan time, and average detector gain. In this embodiment, the DAS gain is modulated using a gain factor Gain_Fac defined as:

$$Gain\_Fac = \frac{macro\_row}{base\_macro\_row} \times \left(\frac{kV}{base\_kV}\right)^n \times \frac{mA}{base\_mA} \times \frac{view\_sample\_time}{base\_view\_sample\_time} \times \frac{1}{OVR(macro\_row)} \times Sys\_Fac$$

where:

| | |
|---|---|
| macro_row | is a detector macro row thickness for the scan to be performed; |
| base_macro_row | is a detector macro row thickness for a baseline calibration; |
| kV | is an x-ray tube voltage for the scan to be performed; |
| base_kV | is an x-ray tube voltage for a baseline calibration; |
| mA | is an x-ray tube current for the scan to be performed; |
| base_mA | is an x-ray tube current for a baseline calibration; |

-continued

| | |
|---|---|
| view_sample-time | is a scan time for the scan to be performed; |
| base_view_sample-time | is a scan time for a baseline calibration; |
| OVR(macro_row) | is a DAS overranging value for the detector macro row thickness in the scan to be performed; and |
| n | is an empirically determined parameter. |

Prior to a scan, and typically during CT system installation or an x-ray tube change, an x-ray tube reference signal, Base-Input, is generated. The x-ray tube reference signal then is used to calibrate a system reference signal, Sys_Fac, each time the system is calibrated. The system reference signal is one of the parameters that is used to generate a DAS gain factor Gain_Fac, which is used to identify an appropriate DAS gain from a look-up table stored, for example, in the CT system computer. The selected DAS gain is used during the scan.

By modulating DAS gain as described above, DAS gain is optimized for a plurality of scanning parameters. In addition, the DAS gain is modified for each scan without substantially increasing the processing time.

BRIEF DESCRIPTION OF THE DRAWINGS

FIG. 4 illustrates an exemplary look-up table for determining DAS gain in accordance with one embodiment of the present invention.

DETAILED DESCRIPTION OF THE DRAWINGS

Figure 1:
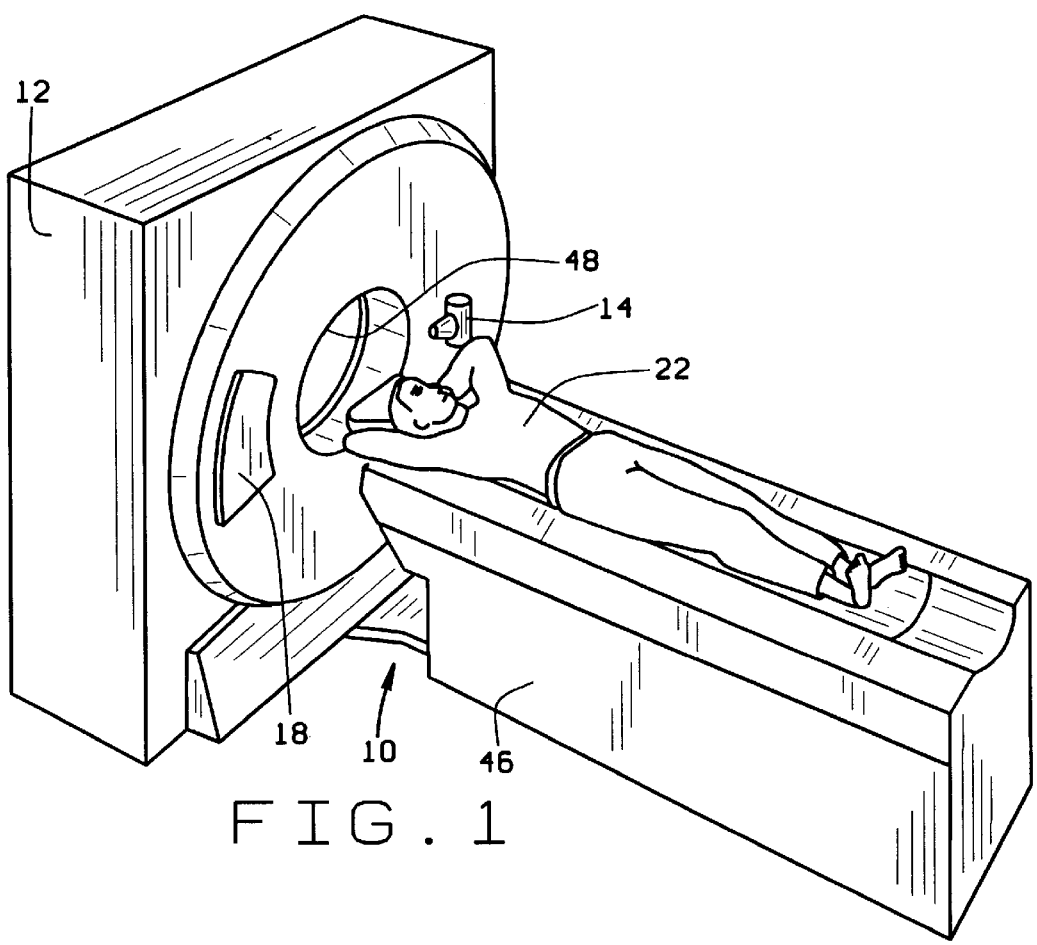
FIG. 1 is a pictorial view of a CT imaging system.
Figure 2:
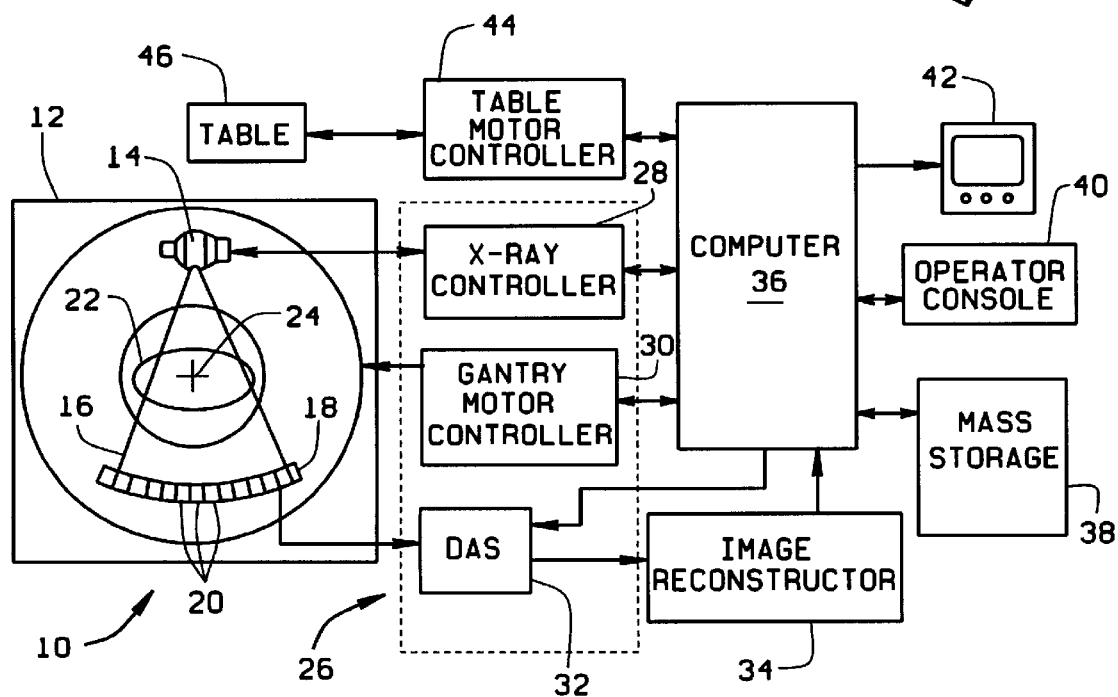
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

While the present DAS gain modulation algorithm is described in accordance with a four slice system, the present modulation is not limited to practice in any particular CT system, nor is such modulation limited to any particular image reconstruction algorithm. Similarly, the present DAS gain modulation is not limited to use in connection with any particular scan type such as helical and axial scans. It should be further understood that the DAS modulation algorithm could be implemented, for example, in computer 36 to control DAS 32 (FIG. 2). In accordance with one embodiment of the present invention, DAS gain for a four slice CT system is modulated based on scanning parameters including x-ray tube current ("mA"), x-ray tube voltage ("kV"), slice thickness ("macro_row"), and scan time ("view_sample_time).

Figure 3:
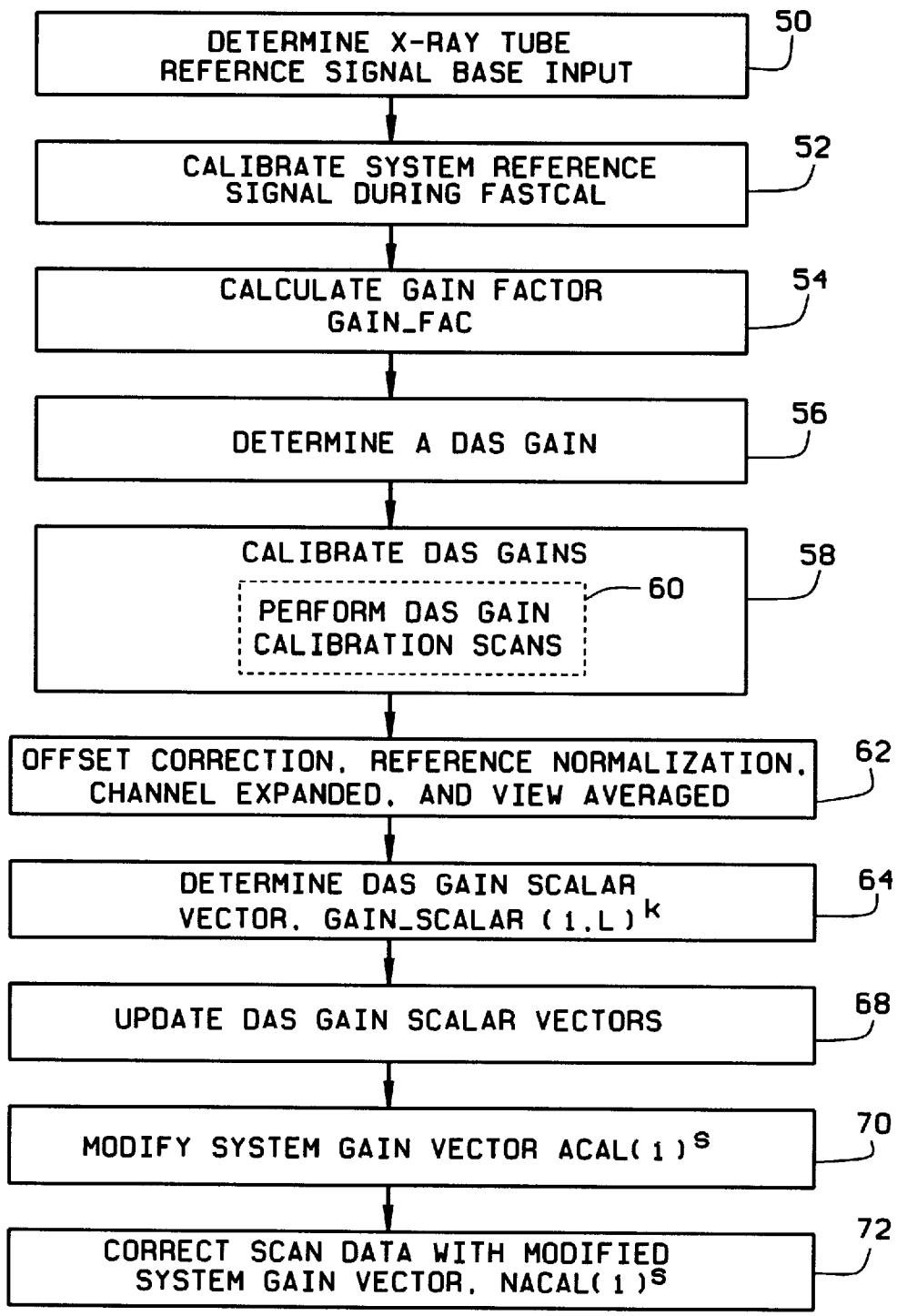
FIG. 3 illustrates a sequence of steps executed for DAS gain calibration and correction in a scan in accordance with one embodiment of the present invention.

Referring to FIG. 3 which illustrates a sequence of steps executed for DAS gain calibration and correction in a scan in accordance with one embodiment of the present invention, an x-ray tube reference signal, Base_Input, is determined 50. Particularly, and during an x-ray tube change, an air scan is performed to generate air scan data, and such air scan data is offset corrected, view averaged, and channel averaged across at least two channels in the center of detector 18 along the x-axis. The air scan data also is averaged over two inner rows of the four slice scanner.

More specifically, the air scan is performed with a maximum x-ray tube current, a maximum x-ray tube voltage, and a 2.5 mm detector macro row thickness at the lowest DAS gain. X-ray tube reference signal Base_Input is then determined in accordance with:

$$\text{Base\_Input} = \frac{1}{\text{Num Views}} \times \frac{1}{\text{Num Chans}} \times \qquad (1)$$

$$\frac{1}{2} \sum_{i=Li}^{n} \sum_{i}^{\text{NumChans}} \sum_{j}^{\text{NumViews}} (X_i(i,j)^0 - \text{OFFSET}i(i,j)^b)$$

where:

| | |
|---|---|
| NumViews | is the number of views averaged; |
| NumChans | is the number of channels averaged; and |
| OFFSET(i,j) | is the offset correction. |

Offset correction algorithms which may be used for OFFSET(i,j) are well known in the art. The determined x-ray tube reference signal, Base_Input, may be stored in a CT system configuration file.

X-ray tube reference signal, Base_Input, is then utilized to calibrate 52 a system reference signal, Sys_Fac which describes relative x-ray tube and detector output variations. Sys_Fac may be described in accordance with:

$$Sys\_Fac = \frac{CAL\_\text{Input}}{\text{Base\_Input}} \qquad (2)$$

where:

| CAL_Input | is a calibration factor. |

CAL_Input is determined in accordance with equation (1), e.g., using substantially the same scanning parameters, each time calibration is performed to monitor x-ray tube output level and average detector gain variation.

Referring again to FIG. 3, a gain factor Gain_Fac is determined 54 utilizing system reference signal Sys_Fac and other parameters such as x-ray tube reference signal Base_Input. Particularly, gain factor Gain_Fac is determined in accordance with scan technique, detector macro row thickness, maximum overrange allowed, and the relative x-ray tube and detector output level in accordance with:

$$\text{Gain\_Fac} = \frac{\text{macro\_row}}{\text{base\_macro\_row}} \times \left(\frac{kV}{\text{base\_kV}}\right)^n \times \frac{mA}{\text{base\_mA}} \times \frac{\text{view\_sample\_time}}{\text{base\_view\_sample\_time}} \times \frac{1}{\text{OVR(macro\_row)}} \times \text{Sys\_Fac} \quad (3)$$

where:

| macro_row | is a detector macro row thickness for the scan to be performed; |
| base_macro_row | is a detector macro row thickness for a baseline calibration; |
| kV | is an x-ray tube voltage for the scan to be performed; |
| base_kV | is an x-ray tube voltage for a baseline calibration; |
| mA | is an x-ray tube current for the scan to be performed; |
| base_mA | is an x-ray tube current for a baseline calibration; |
| view_sample-time | is a scan time for the scan to be performed; |
| base_view_sample-time | is a scan time for a baseline calibration; |
| OVR(macro_row) | is a DAS overranging value for the detector macro row thickness in the scan to be performed; and |
| n | is an empirically determined parameter. |

In one embodiment, n=1.5.

Gain factor Gain_Fac is then used to determine a DAS gain 56 for the scan to be performed. Particularly, gain factor Gain_Fac is utilized to identify and select a DAS gain automatically from a look-up table stored in, for example, computer 36. The look-up table specifically includes predetermined DAS gain values for a plurality of differing gain factors. Gain factor Gain_Fac is then stored, for example, in a scan data file. An exemplary look-up table is set forth in FIG. 4.

DAS gains are then calibrated 58. Particularly, a complete set of DAS gain calibration scans are performed 60 during CT system installation and during each x-ray tube change. Particularly, a baseline DAS gain scan is repeated whenever calibration is performed. For example, each baseline DAS gain scan is an air scan of a 4×2.5 mm slice performed with a body bowtie, a 140 kV x-ray tube voltage, a 380 mA x-ray tube current, a two (2) second scan time, and a DAS gain with $C_{int}$=290 pF. Each baseline DAS gain scan is utilized to generate calibration factor CAL_Input, and accordingly, as described above, to determine system reference signal Sys_Fac. Similarly, the baseline scan parameters, e.g., x-ray tube voltage, x-ray tube current, and scan slice, are used to determine gain factor Gain_Fac.

Raw DAS gain calibration scan data is then offset corrected, reference normalized, channel expanded and cross-talk corrected 62 utilizing substantially the same process as ACAL vector generation in Air CAL. Particularly, for each view j, a vector $X_l(i,j)^k$ is produced for an ith channel in lth row at kth DAS gain. Accordingly, a view averaged gain vector $g_l(i)^k$ is determined in substantially the same way as the ACAL vector is generated from Air calibration, i.e., $$g_l(i)^k = \text{NumViews} \times \frac{1.0}{\sum_{j=1}^{\text{NumViews}} X_l(i,j)^k} \quad (4)$$

where:

$i$ = channel number; and
$l$ = row number.

Subsequently, a DAS gain. scalar vector Gain_scalar(i,j)$^k$ is determined 64 utilizing the baseline DAS gain vector. Particularly, where $g_l(i)^0$ is the gain vector of the baseline DAS gain, DAS gain scalar vector Gain_scalar(i,j)$^k$ at kth DAS gain is determined in accordance with:

$$\text{Gain\_Scalar }(i,l)^k = \frac{g_l(i)^k}{g_l(i)^0} = \frac{(DAS\_GAIN(i,l)/DAS\_GAIN(REF))^0}{(DAS\_GAIN(i,l)/DAS\_GAIN(REF))^k} \quad (5)$$

As shown in equation (5), DAS gain scalar vector Gain scalar(i,j)$^k$ is a ratio of different DAS gain ranges normalized by corresponding DAS gain factors of the reference channel (REF). The DAS gain scalar vectors for all predetermined DAS gains for all data channels may be stored, for example, in a calibration database. Accordingly, each scan file will include a DAS gain scalar vector for the DAS gain used in image scan data collection.

After initially calibrating the system as described above, and in accordance with one embodiment of the invention, each DAS gain scalar vector Gain_scalar(i,j)$^k$ is updated 66. Particularly, and whenever calibration is conducted, two DAS gain calibration scans for each DAS gain in the look-up table and the baseline DAS gain are performed, and the corresponding DAS gain scalar vector Gain_scalar(i,j)$^k$ is updated, i.e., recalculated, as described above. Different DAS gain scalar vectors Gain_scalar(i,j)$^k$ are updated each time a FASTCAL is conducted so that the DAS gain scalar vectors Gain_scalar(i,j)$^k$ are substantially "refreshed".

Scan data acquired during an image scan is then corrected by modifying 68 system gain vector ACAL(i)$^s$ utilizing DAS gain scalar vectors Gain_scalar(i,j)$^k$ for corresponding slices s. Particularly, system gain vector ACAL(i)$^s$ is modified to generate a new system gain vector NACAL(i)$^k$ in accordance with:

$$NACAL(i)^k = ACAL(i)^S \times \frac{\text{Gain\_scaler}(i,l)^k}{\text{Gain\_scaler}(i,l)^S} \quad (6)$$

The system gain vector ACAL(i)$^s$ may be extracted, for example, from a CAL database and stored, for example, in an image scan file. It is to be understood that new system gain vector NACAL(i)$^k$ may be generated for each detector slice in either a single or a multislice detector.

The new system gain vector NACAL(i)$^k$ is then utilized to correct 70 scan data acquired during the image scan. Specifically, correction is performed with the new system gain vector NACAL(i)$^k$ in substantially the same was as normal scan data ACAL correction.

The above described algorithm facilitates optimizing DAS gain for a plurality of scanning parameters. In addition, such algorithm substantially improves low signal performance and reduces DAS overranging. Furthermore, the DAS gain is optimized for each scan without substantially increasing the processing time.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used. For example, the algorithm was described above in a static mode, however, the algorithm may be utilized dynamically during patient scanning. Accordingly, the spirit and scope of the invention are to be limited only by the terms of the appended claims.

What is claimed is:

1. A method for modulating data acquisition system gain in a computed tomography system and correcting data acquired during a system scan, the system including a data acquisition system, an x-ray tube and a detector, the detector including at least one slice of detectors, said method comprising the steps of:

monitoring at least one data acquisition system parameter;

generating a data acquisition gain factor based on the monitored data acquisition system parameter; and modulating data acquisition gain using the generated data acquisition gain factor.

2. A method in accordance with claim 1 wherein monitoring at least one data acquisition system parameter comprises the step of determining at least one of an x-ray tube voltage and an x-ray tube current.

3. A method in accordance with claim 1 wherein monitoring at least one data acquisition system parameter comprises the step of determining at least one of a detector thickness and a scan time.

4. A method in accordance with claim 1 wherein generating a data acquisition gain factor comprises the steps of:

determining an x-ray tube reference signal; and calibrating a system reference signal using the x-ray tube reference signal.

5. A method in accordance with claim 1 further comprising the steps of:

identifying a data acquisition system gain;

calibrating the data acquisition system gain to generate a data acquisition system gain scalar vector; and correcting the scan data utilizing the data acquisition system gain scalar vector.

6. A method in accordance with claim 5 wherein correcting the scan data comprises the steps of:

modifying a system gain vector utilizing the data acquisition system gain scalar vector; and applying the modified system gain vector to the scan data.

7. A system for modulating data acquisition system gain in a computed tomography system and correcting data acquired during a system scan, the computed tomography system including a data acquisition system, an x-ray tube and a detector, the detector including at least one slice of detectors, said system configured to:

monitor at least one data acquisition system parameter;

generate a data acquisition gain factor based on the monitored data acquisition system parameter; and modulating data acquisition gain using the generated data acquisition gain factor.

8. A system in accordance with claim 7 wherein to monitor at least one data acquisition system parameter, said system is configured to determine at least one of an x-ray tube voltage and an x-ray tube current.

9. A system in accordance with claim 7 wherein to monitor at least one data acquisition system parameter, said system is configured to determine at least one of a detector thickness and a scan time.

10. A system in accordance with claim 7 wherein to generate a data acquisition gain factor, said system is configured to:

determine an x-ray tube reference signal; and calibrate a system reference signal using the x-ray tube reference signal.

11. A system in accordance with claim 7 further configured to:

identify a data acquisition system gain;

calibrate the data acquisition system gain to generate a data acquisition system gain scalar vector; and correct the scan data utilizing the data acquisition system gain scalar vector.

12. A system in accordance with claim 11 wherein to correct the scan data, said system is configured to:

modify a system gain vector utilizing the data acquisition system gain scalar vector; and apply the modified system gain vector to the scan data.

13. A system for modulating data acquisition system gain in a computed tomography system and correcting data acquired during a system scan, the computed tomography system including a data acquisition system, an x-ray tube and a detector, the detector including at least one slice of detectors, said system configured to:

monitor at least one of an x-ray tube voltage and an x-ray tube current parameter;

generate a data acquisition gain factor based on the monitored parameter; and modulating data acquisition gain using the generated data acquisition gain factor.

14. A system in accordance with claim 13 wherein said system is further configured to determine at least one of a detector thickness and a scan time.

15. A system in accordance with claim 13 wherein to generate a data acquisition gain factor, said system is configured to:

determine an x-ray tube reference signal; and calibrate a system reference signal using the x-ray tube reference signal.

16. A system in accordance with claim 13 further configured to:

identify a data acquisition system gain;

calibrate the data acquisition system gain to generate a data acquisition system gain scalar vector; and correct the scan data utilizing the data acquisition system gain scalar vector.

17. A system in accordance with claim 16 wherein to correct the scan data, said system is further configured to:

modify a system gain vector utilizing the data acquisition system gain scalar vector; and apply the modified system gain vector to the scan data.

* * * * *